(12) United States Patent
Ahmad et al.

(10) Patent No.: US 8,425,923 B2
(45) Date of Patent: Apr. 23, 2013

(54) LOTION COMPOSITION FOR PERSONAL USE

(75) Inventors: Nawaz Ahmad, Monmouth Junction, NJ (US); Michael Joyce, Randolph, NJ (US); Bartley D. Maxon, St. Louis, MI (US); Thomas E. Jacobs, Bay City, MI (US)

(73) Assignee: Dow Corning Corporation and McNeil-PPC, Inc., Skillman, NJ (US)

( * ) Notice: Subject to any disclaimer, the term of this patent is extended or adjusted under 35 U.S.C. 154(b) by 51 days.

(21) Appl. No.: 12/174,184

(22) Filed: Jul. 16, 2008

(65) Prior Publication Data

US 2008/0275137 A1  Nov. 6, 2008

Related U.S. Application Data

(63) Continuation-in-part of application No. 12/028,347, filed on Feb. 8, 2008, now abandoned.

(60) Provisional application No. 60/889,068, filed on Feb. 9, 2007.

(51) Int. Cl.
*A61Q 19/00* (2006.01)
*A61K 31/695* (2006.01)

(52) U.S. Cl.
USPC .......................................... 424/400; 514/63

(58) Field of Classification Search .................. None
See application file for complete search history.

(56) References Cited

U.S. PATENT DOCUMENTS

| | | | |
|---|---|---|---|
| 4,981,686 A | 1/1991 | Hardy | |
| 5,393,526 A * | 2/1995 | Castro | 424/401 |
| 5,420,118 A | 5/1995 | Alban et al. | |
| 5,654,362 A | 8/1997 | Schulz, Jr. et al. | |
| 5,747,430 A | 5/1998 | Matsushita et al. | |
| 5,885,591 A | 3/1999 | Ahmad et al. | |
| 5,980,924 A | 11/1999 | Yamazaki et al. | |
| 6,060,546 A * | 5/2000 | Powell et al. | 524/267 |
| 6,139,848 A | 10/2000 | Ahmad et al. | |
| 6,262,170 B1 * | 7/2001 | Kilgour et al. | 524/731 |
| 6,271,295 B1 | 8/2001 | Powell et al. | |
| 6,632,420 B1 * | 10/2003 | Cen et al. | 424/65 |
| 6,641,825 B2 | 11/2003 | Scholz et al. | |
| 6,861,061 B2 * | 3/2005 | Maxon et al. | 424/400 |
| 7,005,408 B2 | 2/2006 | Ahmad et al. | |
| 7,255,869 B2 | 8/2007 | Uchida et al. | |
| 7,405,186 B2 | 7/2008 | Harrison | |
| 7,407,666 B2 | 8/2008 | Tarletsky et al. | |
| 7,417,013 B2 | 8/2008 | Ahmad et al. | |
| 2004/0138074 A1 | 7/2004 | Ahmad et al. | |
| 2005/0002976 A1 | 1/2005 | Wu | |
| 2005/0048090 A1 | 3/2005 | Rau | |
| 2005/0058674 A1 | 3/2005 | Joseph et al. | |
| 2005/0089537 A1 | 4/2005 | Birnholz | |
| 2006/0039886 A1 | 2/2006 | Shefer et al. | |
| 2006/0189493 A1 | 8/2006 | Chuah et al. | |
| 2006/0269500 A1 | 11/2006 | Riemer et al. | |
| 2007/0020217 A1 | 1/2007 | Themens | |
| 2007/0135379 A1 | 6/2007 | Mallard et al. | |
| 2008/0194705 A1 | 8/2008 | Ahmad et al. | |

OTHER PUBLICATIONS

The International Cosmetic Ingredient Dictionary and Handbook, eds. Wenninger and McEwen; pp. 1656-1661, 1626, 1654-1655 and 1673-1686. The Cosmetic, Toiletry, and Fragrance Assoc., Washington, D.C. 7$^{th}$ Edition, 1997.

International Search Report dated Jan. 12, 2010 for corresponding International application PCT/US2008/053453.

* cited by examiner

*Primary Examiner* — Jyothsna Venkat

(57) ABSTRACT

This invention relates to emulsion compositions that can warm on contact with ambient moisture and can be used as lubricants on the skin of a person. They may be formulated in the form of a lotion and maintain stability for a significant period of time.

11 Claims, No Drawings

LOTION COMPOSITION FOR PERSONAL USE

CROSS REFERENCE TO RELATED APPLICATIONS

This is a continuation-in-part of application Ser. No. 12/028,347, filed on Feb. 8, 2008, now abandoned which claims the benefit 60/889,068, filed on Feb. 9, 2007, which are hereby incorporated by reference in their entirety.

FIELD OF THE INVENTION

This invention relates to personal care emulsion compositions that may be utilized as personal lubricants prior to or during sexual intercourse as well as massage or moisturizing compositions.

BACKGROUND OF THE INVENTION

In recent years, personal lubricant compositions have been increasingly utilized in the realm of enhancing intimate relationships and assisting couples in the pursuit of intimate activities, including sexual intercourse. Recently, personal lubricant products that are warming and non-irritating were introduced to the market and have been used not only to provide lubrication so as to enable comfortable sexual intercourse, but to enhance the experience associated therewith. They have also been used as massage compositions to help couples connect intimately and set the mood for intimate experiences.

While the warming attribute of personal lubricants such as those described in U.S. Pat. No. 7,005,408 is a positive, desirable one, most warming personal lubricants are clear gels or liquids. As the warming phenomenon is related to exposing a substantially anhydrous composition to ambient moisture, these products are composed almost entirely of one phase which is essentially water-soluble.

Many traditional skin massage compositions are oil products. They promote the distribution of oils to the skin of the individual receiving a massage so as to ease the process of massaging. They may also be in the form of lotions or emulsions that contain both aqueous and oil phases.

Emulsion-based body lotions and massage lotions form a huge segment of the skin care and personal care market. Although the number of such products is quite large, they are primarily designed to function as moisturizers. They are not intended nor designed to be used as personal lubricants. As these emulsions contain, for the most part, an aqueous phase, they are initially cold to the touch and quite uncomfortable upon first application to the skin. Furthermore, many contain emulsifying agents that may be irritating to mucosal tissue and, therefore, would not be appropriate or safe for use as "personal" or vaginal lubricants.

Because emulsion-based creamy lotions are found to be aesthetically pleasing, it is desirable that a massage/personal lubricant composition be created that is in the lotion or emulsion form and will not have the disadvantage of feeling cold upon initial application.

Surprisingly, we have found that providing compositions that may be used as both massage lotions and personal lubricants may be made in the form of emulsions.

SUMMARY OF THE INVENTION

This invention relates to lotion emulsion compositions that can warm on contact with ambient moisture and can be used as lubricants on the skin of a person.

As used herein, the term "emulsion" means a fluid consisting of a microscopically heterogeneous mixture of at least two normally immiscible liquid phases, in which one liquid forms minute droplets suspended in the other liquid. A phase in which the droplets are suspended is referred to as the "continuous" phase. A phase which forms minute droplets is referred to as the "discontinuous" phase. "Oil" is defined as a liquid not miscible with water, generally combustible and soluble in ether. Oils may include both hydrocarbon-based materials as well as silicone-based materials.

The compositions of this invention are preferably emulsion compositions containing at least two phases, at least one continuous phase and at least one discontinuous phase. In at least a first phase of the emulsion, the compositions contain a substantially anhydrous composition containing at least one polyol. In at least a second phase of the emulsion, the compositions contain an oil.

When the emulsion compositions of this invention are applied topically to the skin or mucosal tissue of an individual, they may generate a sensation such as warming in the individual to which they have been applied. Surprisingly, they not only exist in the form of an emulsion, they are extremely lubricious and warm upon application to the skin or mucosa. The compositions of this invention have a lubricity as measured by the method set forth in U.S. Pat. No. 5,885,591 of at least about 33.

The invention is further directed to compositions such as glycol-in-oil emulsions having a discontinuous glycol phase dispersed in a continuous oil phase. The continuous oil phase of the glycol-in-silicone emulsion contains a linear silicone polyether, and combination of silicone fluids and or silicone elastomers. The continuous oil phase of the glycol-in-silicone emulsion may include one or more solvents such as octamethylcyclotetrasiloxane, decamethylcyclopentasiloxane, dodecamethylcyclohexasiloxane, hexamethyldisiloxane, octamethyltrisiloxane, decamethyltetrasiloxane, dodecamethylpentasiloxane, tetradecamethylhexasiloxane, and hexadecamethylheptasiloxane.

These and other features of the invention will become apparent from a consideration of the detailed description.

DETAILED DESCRIPTION OF PREFERRED EMBODIMENTS

The compositions according to this invention contain a polyol in at least one phase of the emulsion.

Preferably, the compositions of this invention contain at least one polyol. Preferably, the polyol is a polyhydric alcohol, and more preferably, the compositions of this invention contain at least two polyhydric alcohols. Polyethylene glycol (hereinafter, "PEG") ethers may also be used, including PEG ethers of propylene glycol, propylene glycol stearate, propylene glycol oleate and propylene glycol cocoate and the like. Specific examples of such PEG ethers include PEG-25 propylene glycol stearate, PEG-55 propylene glycol oleate and the like. Preferably, at least one of the polyhydric alcohols of the compositions of this invention is a polyalkylene glycols or others selected from the following group: glycerine, propylene glycol, butylenes glycol, hexylene glycol or polyethylene glycol of various molecular weight and the like and/or combination thereof. More preferably, the compositions of this invention contain a polyethylene glycol; most preferably, the polyethylene glycol may be selected from the following group: polyethylene glycol 400 or polyethylene glycol 300. Polypropylene glycol of various molecular weights may also be used. PEGylated compounds such as peptide or protein derivatives obtained through PEGylation reactions may also be used. In addition, block copolymers of PEG's may be used, such as (ethylene glycol)-block-poly(propylene glycol)-block-(polyethylene glycol), poly(ethylene glycol-ran-propylene glycol) and the like. The compositions of this invention should contain polyhydric alcohols in an amount from about 70% to about 98% by weight of the composition.

The term "substantially anhydrous" means that the pertinent phase of the composition of this invention contains less than about 20% by weight of water. More preferably, the compositions of this invention contain less than about 15% by weight of water or less than about 10% by weight of water. Most preferably, the substantially anhydrous phase of the composition of this invention contains less than about 5% by weight of water.

Preferably, the substantially anhydrous phase of the compositions of this invention contain at least two polyols. More preferably, a first such polyol should be selected from glycerine and propylene glycol and a second such polyol should be a polyethylene glycol. Most preferably, the substantially anhydrous phase of the compositions of this invention should contain propylene glycol, polyethylene glycol, at least one salt and at least one co-emulsifier. The salt and co-emulsifier provide physical stability to the composition by facilitating the formation of smaller discontinuous phase particles within the composition. Most preferably, the salt should be soluble in polyols and capable of increasing the surface tension of the polyols. The compositions set forth in U.S. Pat. No. 7,005,408 may be used in the substantially anhydrous phases of the compositions of this invention and are hereby incorporated herein by reference. The polyol may be utilized either in a continuous or a discontinuous phase and should still operate to cause warming upon topical application to a person. Most preferably, the polyol is polyethylene glycol 400.

Preferably, the ratio of oil to water in an oil-in-water emulsion of this invention is such that, when water is in a continuous phase, it composes a much higher concentration as compared with the oil portion of the emulsion. More preferably, in oil-in-water compositions of this invention, they should contain from about 20 to about 40% oil and from about 60 to about 80% water. In a water-in-oil emulsion, the reverse is true.

The type of emulsion composition of this invention (i.e., whether it is an oil-in-water or water-in-oil emulsion) also depends upon the hydrophilic-lipophilic balance ("HLB") of the emulsifying surfactant utilized in the compositions of this invention. For an oil-in-water emulsion, the HLB of the surfactant is preferably between about 8 and about 16. Tween 60 (polysorbate 60), for example, is approximately 15 and may be utilized (as may like emulsifying agents) in oil-in-water emulsions for emulsification and stabilization purposes. For a water-in-oil emulsion, the composition should contain a surfactant (also known as an emulsifying agent) having an HLB of from about 3.5 to about 8.

Preferably, the oil phase of the compositions of this invention that constitute oil-in-water or water-in-oil compositions (as opposed to glycol-in-silicone compositions) should contain oil, or "emollient" ingredients as well as emulsifying agents. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. The International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "INCI Handbook") contains numerous examples of suitable materials.

The topical compositions useful in this invention are preferably formulated as emulsions. If the carrier is an emulsion, from about 1% to about 10% (preferably from about 2% to about 5%) of the carrier should be made up of one or more emulsifiers. Emulsifiers may be nonionic, anionic or cationic. Suitable emulsifiers may be found in, for example, the INCI Handbook, pp. 1673-1686.

Lotions and creams may also be formulated as emulsions. Typically such lotions preferably contain from 0.5% to about 5% of an emulsifier(s). Such creams would typically comprise from about 1% to about 20% (preferably from about 5% to about 10%) of an emollient(s); from about 20% to about 80% (preferably, from 30% to about 70%) of water (for oil-in-water or water-in-oil compositions); and from about 1% to about 10% (preferably, from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type are also useful in the subject invention. In general, such single or multiphase emulsions contain water, emollients, and emulsifiers as essential ingredients.

The oil ingredients that may be present in the compositions of this invention preferably include the following: fatty alcohols, glyceryl esters and non-aqueous surfactant liquids that may serve as emulsifiers. Oil ingredients may, in the case of glycol-in-silicone compositions, include silicone-based fluids.

Fatty alcohols may preferably be included in the compositions of this invention. Fatty alcohols are higher molecular weight, nonvolatile, primary alcohols having the general formula: $RCH_2OH$ wherein R is a $C_{8-20}$ alkyl. They can be produced from natural fats and oils by reduction of the fatty acid COOH— grouping to the hydroxyl function. Alternatively, identical or similarly structured fatty alcohols can be produced according to conventional synthetic methods known in the art. Suitable fatty alcohols include, but are not limited to, behenyl alcohol, $C_{9-11}$ alcohols, $C_{12-13}$ alcohols, $C_{12-15}$ alcohols, $C_{12-16}$ alcohols, $C_{14-15}$ alcohols, caprylic alcohol, cetearyl alcohol, coconut alcohol, decyl alcohol, isocetyl alcohol, isostearyl alcohol, lauryl alcohol, oleyl alcohol, palm kernel alcohol, stearyl alcohol, cetyl alcohol, tallow alcohol, tridecyl alcohol or myristyl alcohol. Preferably, the oil phase of the compositions of this invention contain fatty alcohols having a carbon chain from about 18 to about 20 and more preferably, having a carbon chain containing about 18 carbons, such as stearyl alcohol.

Glyceryl esters may also be preferably included in the compositions according to this invention. They comprise a subgroup of esters which are primarily fatty acid mono- and di-glycerides or triglycerides modified by reaction with other alcohols and the like. Preferred glyceryl esters are mono and diglycerides. Suitable glyceryl esters and derivatives thereof include, but are not limited to, acetylated hydrogenated tallow glyceride, glyceryl behenate, glyceryl caprate, glyceryl caprylate, glyceryl caprylate/caprate, glyceryl dilaurate, glyceryl dioleate, glyceryl erucate, glyceryl hydroxystearate, glyceryl isostearate, glyceryl lanolate, glyceryl laurate, glyceryl linoleate, glyceryl oleate, glyceryl stearate, glyceryl myristate, glyceryl distearate and mixtures thereof. More preferably, glyceryl stearate is utilized in the compositions of this invention.

Additional ingredients may be added to the oil-in-water emulsions as emulsion stabilizers. Such emulsion stabilizers may also be added to the glycol-in-silicone compositions of this invention as well. For example, cellulose derivatives, (including cellulosic polymers such as hydroxyalkylcelluloses) and salts, including sodium chloride, potassium chloride, and other inorganic salts soluble in polyols may act as emulsion stabilizers and preferably reside in the glycol phase of the emulsion.

Preferably, such cellulosic polymers include carboxymethylcellulose, hydroxyethylcellulose, hydroxypropycellulose and hydroxypropylmethylcellulose. The preferred emulsion stabilizing agent, however, is hydroxylpropylcellulose. Another potential emulsion stabilizing agent is a cross-linked acrylic acid-based polymer such as a carbopol. A carbopol may be present in the oil-in-water compositions of this invention in an amount of from about 0.2% to about 2% by weight of the composition.

Suitable types of non-aqueous surfactant liquids which can be used to form the oil phase of the personal lubricant-massage compositions of this invention include the alkoxylated alcohols, ethylene oxide (EO)-propylene oxide (PO) block polymers, polyhydroxy fatty acid amides, alkylpolysaccharides, and the like. Such normally liquid surfactants are those having a hydrophilic-lipophilic balance ("HLB") ranging from about 10 to about 16. "HLB" is defined as a measure of the degree to which it is hydrophilic or lipophilic, as determined by calculating values for the different regions of the molecule. Most preferred of the surfactant liquids is polyethylene glycol sorbitan monostearate, other surfactants having an HLB of about 12 to about 15, and other surfactants having an HLB for about 15.

In one preferred embodiment of the compositions of this invention, an anhydrous polyol phase is present in the composition as a continuous phase of the emulsion and an oil phase is present in the composition as the discontinuous phase.

More preferably, in this approach, the "aqueous" or substantially anhydrous polyol phase contains from about 10 to about 15% water is used as an aqueous phase of the emulsion and the polyol phase further contains from about 70 to about 80% of a combination of polyols. More preferably, a combination of propylene glycol and polyethylene glycol a ratio of from about 1 to about 3 should be present in the polyol phase. Preferably, the "oil" or lipophilic phase of the emulsion should contain from about 5 to about 10% of stearyl alcohol and from about 1 to about 5% of glyceryl stearate as the oil phase of the emulsion, from about 1 to about 3% of polyethylene glycol sorbitan monostearate is used as an emulsifier, from about 0.1% to about 2% carbopol alone or in combination with from about 0.1 to about 2% of hydroxyethylcellulose may be used as emulsion stabilizers. To these, could be added 0.5 to 5% Silicone Fluid, 350 cst, as a lubricant and 0.1% to 0.5% benzoic acid as a preservative. The continuous phase of these emulsions is water, propylene glycol and polyethylene glycol combination and the dispersed or the discontinuous phase is the oil phase comprising stearyl alcohol and glyceryl stearate. Polysorbate 60 is preferably the emulsifier.

This invention is also related to compositions and methods of incorporating warming ingredients into glycol-in-silicone oil emulsions. In particular, the invention involves the use of a generally linear silicone polyether as the silicone emulsifier, in combination with other silicones and warming ingredients to achieve an anhydrous warming lotion. A co-emulsifier that is soluble with the glycol phase of the glycol-in-silicone oil emulsion is preferably present in the composition. Preferably, the co-emulsifier is a non-ionic emulsifier from the general class of polyoxyethylene sorbitan fatty acid esters. In addition, an emulsion stabilizer, such as a salt soluble in polyols, may be incorporated into the glycol phase of the emulsion.

The following sections relate more specifically to preferred compositions relating to glycol-in-silicone oil emulsions of this invention.

The Linear (i.e., Non-Crosslinked, Silicone Polyether)

The linear (i.e., non-crosslinked, silicone polyether) used to prepare compositions according to this invention, is generally dispersible in the oil phase. It can have a rake type structure wherein the polyoxyethylene or polyoxyethylene-polyoxypropylene copolymeric units are grafted onto the siloxane backbone, or the SPE can have an ABA block copolymeric structure wherein A represents the polyether portion and B the siloxane portion of an ABA structure.

Non-crosslinked silicone polyethers suitable for use herein have the formula $MD_{0-1,000}D'_{1-100}M$, most preferably the formula $MD_{0-500}D'_{1-50}M$, where M represents monofunctional unit $R_3SiO_{1/2}$, D represents difunctional unit $R_2SiO_{2/2}$, and D' represents difunctional unit $RR'SiO_{2/2}$. In these formulas, R is an alkyl group containing 1-6 carbon atoms or an aryl group, and R' is an oxyalkylene containing moiety. The R' groups may contain only oxyethylene (EO) units; a combination of oxyethylene (EO) and oxypropylene (PO) units; or a combination of oxyethylene (EO) units, oxypropylene (PO) units, and oxybutylene (BO) units. Preferred R' groups include oxyalkylene units in the approximate ratio of $EO_{3-100}PO_{0-100}$, most preferably in the ratio $EO_{3-30}PO_{1-30}$.

R' moieties typically include a divalent radical such as —$C_mH_{2m}$— where m is 2-8 for connecting the oxyalkylene portion of R' to the siloxane backbone. Such moieties also contain a terminating radical for the oxyalkylene portion of R' such as hydrogen, hydroxyl, or an alkyl, aryl, alkoxy, or acetoxy group.

Non-crosslinked silicone polyethers useful herein can also be of a type having the formula $M'D_{10-1,000}D'_{0-100}M'$, most preferably the formula $M'D_{10-500}D'_{0-50}M'$, wherein M' represents monofunctional unit $R_2R'SiO_{1/2}$, D represents difunctional unit $R_2SiO_{2/2}$, and D' represents difunctional unit $RR'SiO_{2/2}$. In these formulas, R can be an alkyl group containing 1-6 carbon atoms or an aryl group, and again R' represents an oxyalkylene containing moiety. As noted previously, R' groups typically contain only oxyethylene (EO) units or combinations of oxyethylene (EO) and oxypropylene (PO) units. Such R' groups include these oxyalkylene units in the ratio $EO_{3-100}PO_{0-100}$, most preferably $EO_{3-30}PO_{1-30}$.

As also noted previously, R' moieties typically include a divalent radical —$C_mH_{2m}$— where m is 2-8 for connecting the oxyalkylene portions of R' to the siloxane backbone.

In addition, the moiety R' contains a terminating radical for oxyalkylene portions of R' such as hydrogen, hydroxyl, an alkyl, aryl, alkoxy, or acetoxy group.

In addition, non-crosslinked silicone polyethers useful herein can having the formula $MD_{0-1,000}D'_{0-100}D''_{1-1,00}M$ wherein D" represents difunctional unit $RR''SiO_{2/2}$, and R" is an alkyl group containing 1-40 carbon atoms. M, D, D', and R, are the same as defined above.

Table 1 shows some representative linear, i.e., non-crosslinked, silicone polyethers conforming to these formulas which can be used in preparing emulsions according to the invention.

TABLE 1

Linear Silicone Nominal Structure of Linear, i.e., Non-Crosslinked, Silicone Polyether Polyether A $MD_{8.6}D'_{3.6}M$ where R is- —$CH_3$ and R' is- —$(CH_2)_3(EO)_{12}OH$
B $MD_{108}D'_{10}M$ where R is- —$CH_3$ and R' is- —$(CH_2)_3(EO)_{10}(PO)_4OH$ TABLE 1-continued Linear Silicone Nominal Structure of Linear, i.e., Non-Crosslinked, Silicone Polyether Polyether CM'D'$_{75}$M' where R is- —CH$_3$ and R' is - —(CH$_2$)$_3$(EO)$_{18}$(PO)$_{18}$OAc
DM'D'$_{50}$M' where R is- —CH$_3$ and R' is- —(CH$_2$)$_3$(EO)$_{18}$(PO)$_{18}$OH
EM'D'$_{13}$M' where R is- —CH$_3$ and R' is- —(CH$_2$)$_3$(EO)$_{12}$OH
PMD$_{22}$D'$_2$M where R is- —CH$_3$ and R' is - —(CH$_2$)$_3$(EO)$_{12}$(PO)$_{12}$OH
GMD$_{396}$D'$_4$M where R is- —CH$_3$ and R' is- —(CH$_2$)$_3$(EO)$_{18}$(PO)$_{18}$OH The Volatile Silicone, i.e., The Solvent The solvent used herein is a volatile silicone, generally a low molecular weight silicone oil, and most typically a cyclic alkyl siloxane of the formula (R'''$_2$SiO)$_d$ or a linear alkyl siloxane of the formula R'''$_3$SiO(R'''$_2$SiO)$_e$SiR'''$_3$ in which R''' is an alkyl group containing 1-6 carbon atoms, d is 3-6 and e is 0-5. Most preferred, however, are volatile cyclic methyl siloxanes of the formula {(CH$_3$)$_2$SiO}$_d$ and volatile linear methyl siloxanes of the formula (CH$_3$)$_3$SiO{(CH$_3$)$_2$SiO}$_e$Si(CH$_3$)$_3$ and in which d is 3-6 and e is 0-5, respectively. Preferably, the volatile methyl siloxane has a boiling point less than 250° C. and a viscosity of 0.65-5.0 centistoke (mm$^2$/s).

Some representative linear volatile methyl siloxanes are hexamethyldisiloxane (MM) with a boiling point of 100° C., viscosity of 0.65 mm$^2$/s, and formula Me$_3$SiOSiMe$_3$; octamethyltrisiloxane (MDM) with a boiling point of 152° C., viscosity of 1.04 mm$^2$/s, and formula Me$_3$SiOMe$_2$SiOSiMe$_3$; decamethyltetrasiloxane (MD$_2$M) with a boiling point of 194° C., viscosity of 1.53 mm$^2$/s, and formula Me$_3$SiO(Me$_2$SiO)$_2$SiMe$_3$; dodecamethylpentasiloxane (MD$_3$M) with a boiling point of 229° C., viscosity of 2.06 mm$^2$/s, and formula Me$_3$SiO(Me$_2$SiO)$_3$SiMe$_3$; tetradecamethylhexasiloxane (MD$_4$M) with a boiling point of 245° C., viscosity of 2.63 mm$^2$/s, and formula Me$_3$SiO(Me$_2$SiO)$_4$SiMe$_3$; and hexadecamethylheptasiloxane (MD$_5$M) with a boiling point of 270° C., viscosity of 3.24 mm$^2$/s, and formula Me$_3$SiO(Me$_2$SiO)$_5$SiMe$_3$. "Me" in these and the following formulas represents the methyl group CH$_3$.

Some representative cyclic volatile methyl siloxanes are hexamethylcyclotrisiloxane (D$_3$), a solid at room temperature, with a boiling point of 134° C. and formula (Me$_2$SiO)$_3$; octamethylcyclotetrasiloxane (D$_4$) with a boiling point of 176° C., viscosity of 2.3 mm$^2$/s, and formula (Me$_2$SiO)$_4$; decamethylcyclopentasiloxane (D$_5$) with a boiling point of 210° C., viscosity of 3.87 mm$^2$/s, and formula (Me$_2$SiO)$_5$; and dodecamethylcyclohexasiloxane (D$_6$) with a boiling point of 245° C., viscosity of 6.62 mm$^2$/s, and formula (Me$_2$SiO)$_6$.

Non-Volatile Silicone Fluids:

Nonvolatile silicone fluids of the present invention may include those which conform to the formula:

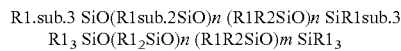
R1$_3$ SiO(R1$_2$SiO)n (R1R2SiO)m SiR1$_3$ where n and m have a value to provide polymers with a viscosity in the range of about 100-1,000 centistokes (mm2/sec).

R1 and R2 are alkyl radicals of 1-20 carbon atoms, or an aryl group such as phenyl. Typically, the value of n is about 80-375. Illustrative polysiloxanes are polydimethylsiloxane, polydiethylsiloxane, polymethylethylsiloxane, polymethylphenylsiloxane, and polydiphenylsiloxane These linear silicone materials may generally have viscosity values of from 5 centistokes or 10 centistokes but no more than about 100,000 centistokes, but preferably in the range of 20 centistokes to 12,500 cst, as measured under ambient conditions. Specific non limiting examples of suitable non-volatile silicone fluids include Dow Corning Q7-9120 Silicone Fluids (Dimethicone NF).

The Silicone Gum

The silicone gum useful in the glycol-in-silicone compositions of this invention is a high molecular weight, most typically a silanol functional polymer, but including polydimethylsiloxane gums as well. Such gums are known in the art and are readily available commercially from vendors such as the Dow Corning Corporation, Midland, Mich. Such materials have a structure generally corresponding to the formula:

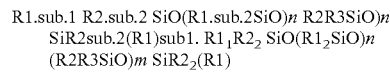
SiR2sub.2(R1)sub1. R1$_1$R2$_2$ SiO(R1$_2$SiO)n (R2R3SiO)m SiR2$_2$(R1)

in which n and m are integers of 5,000-50,000, preferably 10,000-50,000. R1 represents—OH; an alkyl group having 1-6 carbon atoms such as methyl, ethyl, or propyl; an aryl group such as phenyl or xenyl; an alkaryl group such as tolyl or xylyl; or an aralkyl group such as benzyl, phenylethyl, or 2-phenylpropyl. R2 represents an alkyl group having 1-6 carbon atoms such as methyl, ethyl, or propyl; an aryl group such as phenyl or xenyl; an alkaryl group such as tolyl or xylyl; or an aralkyl group such as benzyl, phenylethyl, or 2-phenylpropyl. Silicone gums in which R1 is an alkenyl group such as vinyl can also be employed. Most preferred, however, are silicone gums in which R1 is —OH and R2 is methyl; and in which both R1 and R2 are methyl.

α,ω-Diene Crosslinked Silicone Elastomer

As used herein, the term α,ω-diene crosslinked silicone elastomer is intended to mean α,ω-diene crosslinked silicone elastomers having no oxyalkylene units in their structure. They have been referred to generally in the art as non-emulsifying silicone elastomers, meaning that polyoxyalkylene units are absent. Otherwise, the α,ω-diene crosslinked silicone elastomers suitable for use according to this invention are the compositions described in U.S. Pat. No. 5,654,362 (Aug. 5, 1997).

As described in detail in the '362 patent, the α,ω-diene crosslinked silicone elastomers are prepared by reacting (A) an ≡Si—H containing polysiloxane of the formula R$_3$SiO(R'$_2$SiO)$_a$(R"HSiO)$_b$SiR$_3$ and optionally an ≡Si—H containing polysiloxane of formula HR$_2$SiO(R'$_2$SiO)$_c$SiR$_2$H or formula HR$_2$SiO(R'$_2$SiO)$_a$(R"HSiO)$_b$SiR$_2$H where R, R', and R" are alkyl groups with 1-6 carbon atoms; a is 0-250; b is 1-250; and c is 0-250; with (B) an alpha, omega-diene of formula CH$_2$=CH(CH$_2$)$_x$CH=CH 2 where x is 1-20. The reaction is conducted in the presence of a platinum catalyst and in the presence of (C) a low molecular weight silicone oil or other solvent. The reaction system is non-aqueous in contrast to the reaction system used to prepare silicone rubber powders.

The polydiorganosiloxane gums are well known in the art and can be obtained commercially, and which have viscosities greater than 1,000,000 cs. at 25.degree C., preferably greater than 5,000,000 cs. at 25.degree C.

Co-Emulsifiers

Co-emulsifiers useful in the glycol-in-silicone compositions of this invention are emulsifiers that are soluble in the glycol phase. Polyoxyethylene sorbitan fatty acids such as Polysorbate 20 (Polyoxethylene [20] sorbitan monlaurate), Polysorbate 40 (Polyoxethylene [20] sorbitan monopalmitate), Polysorbate 60 (Polyoxethylene [20] sorbitan monostearate), and Polysorbate 80 (Polyoxethylene [20] sorbitan monoleate) are examples of one class of emulsifiers that function in this manner. The number 20 following the term "polyoxyethylene" refers to the total number of oxyethylene groups found in the molecule. The number following the term "polysorbate" refers to the type of fatty acid associated with the polyoxyethylene sorbitan portion of the referenced molecule. "Monolaurate" is indicated by the numeral 20, "monopalmitate" is indicated by the numeral 40, "monostearate" by the numeral 60, and "monooleate" by the numeral 80. Such emulsifiers may be present in the composition in the amount of from about 0.5 to about 2% by weight of the total composition.

Salts

Salts useful in the glycol-in-silicone compositions of this invention are inorganic salts that have solubility in the glycol phase. It has been shown that these salts serve to increase the surface tension of the glycol phase and thereby promote physical stability in the compositions of this invention. Examples of salts that function in this manner include, but are not limited to, sodium chloride, potassium chloride, ammonium chloride, magnesium chloride, calcium chloride, calcium bromide, sodium bromide, sodium acetate, potassium acetate, sodium citrate, or combinations thereof. In the glycol-in-silicone emulsions of this invention, the addition of these salts enhances the physical stability of the emulsion by facilitating the formation of smaller discontinuous phase particles. Preferably, said salt is present in the compositions of this invention in an amount of from about 0.1 to about 1% by weight of the composition.

The compositions according to the invention can be prepared mechanically, and this simply involves mixing the oil phase and the water phase together and homogenizing the phase mixture using a laboratory homogenizer or other device for applying vigorous agitation.

Additional Cosmetically Active Agents

In one embodiment, the compositions according to this invention may further contain one or more additional cosmetically active agent(s) as well as the above-mentioned components. What is meant by a "cosmetically active agent" is a compound, which may be a synthetic compound or a compound isolated, purified or concentrated from a natural source, or a natural extract containing a mixture of compounds, that has a cosmetic or therapeutic effect on the tissue, including, but not limited to: anti-microbial agents such as anti-yeast agents, anti-fungal, and anti-bacterial agents, anti-inflammatory agents, anti-aging agents, anti-parasite agents, external analgesics, antioxidants, keratolytic agents, detergents/surfactants, moisturizers, nutrients, vitamins, minerals, energy enhancers, firming agents, agents for skin or mucosal conditioning, and odor-control agents such as odor masking or pH-changing agents.

In one embodiment, the cosmetically active agent may be selected from, but not limited to, the group consisting of hydroxy acids, benzoyl peroxide, D-panthenol, octyl methoxycinnimate, titanium dioxide, octyl salicylate, homosalate, avobenzone, carotenoids, free radical scavengers, spin traps, retinoids such as retinoic acid (tretinoin) and retinoid precursors such as retinol and retinyl palmitate, vitamins such as vitamin E (alpha, beta or delta tocopherols and/or their mixtures) ceramides, polyunsaturated fatty acids, essential fatty acids, enzymes, enzyme inhibitors, minerals, hormones such as progesterones, steroids such as hydrocortisone, 2-dimethylaminoethanol, metal (including but not limited to iron or zinc) salts such as copper chloride, peptides containing copper such as Cu:Gly-His-Lys, coenzyme Q10, amino acids, vitamins, acetyl-coenzyme A, niacin, riboflavin, thiamin, ribose, electron transporters such as NADH and FADH2, botanical extracts such as aloe vera, Feverfew, and Soy, and derivatives and mixtures thereof. The cosmetically active agent will preferably be present in the composition of the invention in an amount of from about 0.001% to about 20% by weight of the composition, more preferably, from about 0.005% to about 10% and most preferably, from about 0.01% to about 5%.

Examples of vitamins that may be constituents of the compositions of this invention include, but are not limited to, vitamin A, vitamin Bs such as vitamin B3, vitamin B5, and vitamin B12, vitamin C, vitamin K, vitamin E such as alpha, gamma or delta-tocopherol, and derivatives (such as salts and esters) and mixtures thereof.

Examples of antioxidants that may be utilized in the compositions and methods of this invention include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), different types of tocopherols (e.g., alpha-, gamma-, and delta-tocopherols and their esters such as acetate) and their mixtures, tocotrienols, and ubiquinone. Natural extracts containing antioxidants suitable for use in the compositions of this invention, include, but are not limited to, extracts containing flavonoids, isoflavonoids, and their derivatives such as genistein and diadzein (e.g., such as soy and clover extracts, extracts containing resveratrol and the like. Examples of such natural extracts include grape seed, green tea, pine bark, and propolis.

The compositions of the present invention may also comprise chelating agents (e.g., EDTA) and preservatives (e.g., parabens). Examples of suitable preservatives and chelating agents are listed in pp. 1626 and 1654-55 of the INCI Handbook. In addition, the topical compositions useful herein can contain conventional cosmetic adjuvants, such as dyes, opacifiers (e.g., titanium dioxide), pigments, and fragrances.

EXAMPLES

Example 1

Oil-in-Water Emulsions

Oil-in-water emulsions in accordance with this invention may be made as follows: the components of the oil phase (i.e., stearyl alcohol, glyceryl stearate, and silicone fluid) are added to a mixing vessel in the order listed and combined with moderate agitation while heating to 45-65 C. The components of the water phase (i.e, propylene glycol, cetyl hydroxyethylcellulose, purified water, preservative, emulsifier, polyethylene glycol 400, and carbopol) are added to a separate mixing vessel in the order listed and combined with moderate agitation while heating to about 45 to about 65 C. The oil phase is then added to the water phase with sufficient mixing and shear to completely incorporate it into the water phase and form an oil-in-water emulsion having a substantially homogeneous appearance. The pH adjuster is then added and incorporated uniformly throughout the emulsion.

Examples of oil-in-water compositions according to this invention are as follows:

Example 1A

| Ingredient | % w/w |
| --- | --- |
| Polyethylene glycol 400 | 50.00 |
| Propylene glycol | 25.25 |
| Emulsifier | 3.00 |
| Stearyl alcohol | 7.00 |
| Glyceryl stearate | 1.00 |
| Silicone fluid (350 cst) | 0.50 |
| Carbopol | 0.125 |
| PH adjuster | 0.025 |
| Preservative | 0.20 |
| Purified water | 12.90 |
| Total | 100.00 |

Example 1B

| Ingredient | % w/w |
| --- | --- |
| Polyethylene glycol 400 | 50.00 |
| Propylene glycol | 25.15 |
| Emulsifier | 3.00 |
| Stearyl alcohol | 7.00 |
| Glyceryl stearate | 1.00 |
| Silicone fluid (350 cst) | 0.50 |
| Carbopol | 0.125 |
| Cetyl Hydroxyethylcellulose | 0.10 |
| pH adjuster | 0.025 |
| Preservative | 0.20 |
| Purified water | 12.90 |
| Total | 100.00 |

Example 2

Glycol-in-Silicone Emulsions

Glycol-in-silicone emulsions may be prepared as follows: the components of the silicone phase (i.e., silicone fluids, dimethiconol blend, silicone in cyclopentasiloxane, and silicone elastomer blend) are added to a mixing vessel in the order listed and combined with moderate agitation. The components of the glycol phase (i.e, propylene glycol, polyethylene glycol 400, hydroxypropylcellulose, carbopol, polysorbate 20, sodium chloride and antioxidant) are added to a separate mixing vessel and combined with moderate agitation. The glycol phase is then added to the silicone phase at a rate of addition that is sufficiently slow to allow the glycol phase to be completely incorporated into the silicone phase and form a glycol-in-silicone emulsion having a substantially homogeneous appearance.

Examples of glycol-in-silicone emulsions are as follows:

Example 2A

| Ingredient | % w/w |
| --- | --- |
| Polyethylene glycol 400 | 20.20 |
| Propylene glycol | 50.80 |
| Silicone fluids (20 cst, 350 cst) | 1.6 to 5.6 |
| Dimethiconol blend | 2.50 |
| Silicone polyether in cyclopentasiloxane | 20.30 |
| Silicone elastomer blend | 1.60 |
| Lactic Acid | 1.50 |
| Salt | 0.20 |
| Total | 100.00 |

Example 2B

| Ingredient | % w/w |
| --- | --- |
| Polyethylene glycol 400 | 22.90 |
| Propylene glycol | 52.50 |
| Silicone fluid (20, 350 cst) | 1.00 to 2.50 |
| Dimethiconol blend | 0.90 |
| Silicone polyether in cyclopentasiloxane | 20.30 |
| Silicone elastomer blend | 0.50 |
| Hydroxypropylcellulose | 0.30 |
| Carbopol | 0.125 |
| Antioxidant | 0.10 |
| Total | 100.00 |

Example 2C

| Ingredient | % w/w |
| --- | --- |
| Polyethylene glycol 400 | 21.95 |
| Propylene glycol | 50.36 |
| Silicone fluid (20, 1000 cst) | 1.33 to 4.9 |
| Dimethiconol blend | 2.10 |
| Silicone polyether in cyclopentasiloxane | 20.30 |
| Hydroxypropylcellulose | 0.29 |
| Antioxidant | 0.10 |
| Total | 100.00 |

Example 2D

| Ingredient | % w/w |
| --- | --- |
| Polyethylene Glycol 400 | 21.49 |
| Propylene Glycol | 49.32 |
| Silicone Fluid (20 cst, 350 cst) | 4.90 |
| Dimethiconol Blend | 2.10 |
| Silicone polyether in Cyclopentasiloxane | 20.30 |
| Hydroxypropyl Cellulose | 0.29 |
| Polysorbate 20 | 1.00 |
| Sodium Chloride | 0.50 |
| Antioxidant | 0.10 |
| TOTAL | 100.00 |

Example 3

Generation of Warmth Using Warming Compositions of this Invention

The compositions set forth in Examples 1 and 2 above were tested to determine whether they generated warmth upon application to skin. The test method set forth in Example 3 of U.S. Pat. No. 7,005,408 was utilized to determine expected temperature rise when combined with water. The data set forth in Table 2 were generated by mixing 20 ml of each of the compositions of the examples with 20 ml of water. The initial temperature of each (Composition and water) was determined and an average of the two temperatures was calculated. Water was then added to the compositions. After the addition of water, the mixture was mixed for two minutes and the actual temperature was recorded. The Average Temperature was then subtracted from the Actual Temperature, resulting in the "Rise in Temperature".

The results set forth in Table 2 below were obtained, demonstrating that the compositions of this invention would be expected to generate warmth upon application to skin and the ambient moisture located thereon.

TABLE 2

Generation of Warmth Utilizing Compositions of Examples 1 and 2 (Temperature Rise When Mixed With Water)

| Product Name | Temperature of the Product (° F.) | Temperature of Water (° F.) | Average Expected Temperature (° F.) | Actual Temperature (° F.) | Rise in Temperature(° F.) (Expected Minus Actual) |
|---|---|---|---|---|---|
| Oil-in-Water Emulsion Compositions ||||||
| Example 1A | 75.3 | 72.3 | 73.8 | 90.0 | 16.2 |
| Example 1B | 80.0 | 73.2 | 76.6 | 91.0 | 14.4 |
| Glycol-in-Silicone Emulsion Compositions ||||||
| Example 2A | 77.5 | 73.0 | 75.3 | 89.0 | 13.7 |
| Example 2B | 77.7 | 70.9 | 74.3 | 90.5 | 16.2 |
| Example 2C | 78.5 | 69.0 | 73.8 | 87.5 | 13.7 |
| Example 2D | 76.8 | 76.2 | 76.5 | 91.9 | 15.4 |

What is claimed is:

1. A glycol-in-silicone emulsion lubricant composition comprising a discontinuous substantially anhydrous phase dispersed in a continuous oil phase, wherein said phases are mixed and homogenized, wherein the discontinuous substantially anhydrous phase comprises less than 20 percent by weight of water, wherein the continuous oil phase comprises a linear silicone polyether, wherein the linear silicone polyether has a structure selected from the group consisting of (a) a rake type structure wherein the polyoxyethylene or polyoxyethylene-polyoxypropylene copolymeric units are grafted onto a siloxane backbone, and (b) an ABA block copolymeric structure wherein A represents the polyether portion and B represents the siloxane portion of an ABA structure; wherein the continuous oil phase further comprising silicone fluids; and wherein the discontinuous substantially anhydrous phase further comprising two polyols, wherein the first polyol is selected from the group consisting of glycerine and propylene glycol and the second polyol is polyethylene glycol, at least one salt and at least one coemulsifier wherein said composition has a lubricity of at least about 33 wherein the discontinuous substantially anhydrous phase comprises less than about 5% water by weight of the composition.

2. A glycol-in-silicone emulsion lubricant composition according to claim 1 wherein the continuous oil phase comprises about 1.8 to about 3.5 percent by weight of the linear silicone polyether, about 18 to about 27 percent by weight of a volatile silicone solvent, wherein said volatile silicone solvent comprises a volatile cyclic alkyl siloxane with the formula $(R'''_2SiO)_d$ or a volatile linear alkyl siloxane with the formula $R'''_3SiO(R''' 2SiO)_e SiR'''3$ in which R''' is an alkyl group containing 1-6 carbon atoms, d is 3-6 and e is 0-5.

3. The glycol-in-silicone emulsion lubricant composition according to claim 1 wherein the volatile silicone solvent is selected from the group consisting of hexamethylcyclotrisiloxane, octamethylcyclotetrasiloxane, decamethylcyclopentasiloxane, dodecamethylcyclohexasiloxane, octamethyltrisiloxane, hexamethyldisiloxane, decamethyltetrasiloxane, dodecamethylpentasiloxane, tetradecamethylhexasiloxane, and hexadecamethylheptasiloxane.

4. The glycol-in-silicone emulsion lubricant composition according to claim 1 wherein said salt is an inorganic salt soluble in the discontinuous substantially anhydrous phase.

5. The glycol-in-silicone emulsion lubricant composition according to claim 4 wherein said salt is selected from the group consisting of sodium chloride, potassium chloride, ammonium chloride, magnesium chloride, calcium bromide, sodium bromide, sodium acetate, potassium acetate, sodium citrate and combinations thereof.

6. The glycol-in-silicone emulsion lubricant composition according to claim 4, wherein said salt comprises from about 0.1 to about 1% by weight of the composition.

7. The glycol-in-silicone emulsion lubricant composition according to claim 1, wherein the coemulsifier comprises polyoxyethylene sorbitan fatty acids selected from the group consisting of polysorbate 20, polysorbate 40, polysorbate 60, polysorbate 80 and combinations thereof.

8. The glycol-in-silicone emulsion lubricant composition according to claim 7, wherein said co-emulsifier comprises from about 0.5 to about 2% by weight of the composition.

9. A glycol-in-silicone emulsion lubricant composition according to claim 1 wherein said linear silicone polyether is selected from the group consisting of (i) volatile polydimethylsiloxanes selected from the group consisting of hexamethyldisiloxane, octamethyltrisiloxane, and decamethylcyclopentasiloxane; and (ii) nonvolatile polydimethylsiloxanes having a viscosity from about 5 to about 30,000 centistoke ($mm^2/s$).

10. A glycol-in-silicone emulsion according to claim 1 wherein said emulsion further comprises silicone gums.

11. The glycol-in-silicone emulsion lubricant composition according to claim 10 wherein the silicone gums comprise from about 2 to about 10% by weight of the composition.

\* \* \* \* \*